United States Patent
Kasvikis et al.

(10) Patent No.: US 8,016,176 B2
(45) Date of Patent: Sep. 13, 2011

(54) SURGICAL STAPLING INSTRUMENT WITH INDEPENDENT SEQUENTIAL FIRING

(75) Inventors: Dino Kasvikis, Middletown, CT (US); Danyel J. (Tarinelli) Racenet, Middletown, CT (US); David Farascioni, Bethel, CT (US); Thomas Wenchell, Durham, CT (US); Philip C. Roy, Orange, CT (US)

(73) Assignee: Tyco Healthcare Group, LP, New Haven, CT (US)

( * ) Notice: Subject to any disclaimer, the term of this patent is extended or adjusted under 35 U.S.C. 154(b) by 235 days.

(21) Appl. No.: 12/430,199

(22) Filed: Apr. 27, 2009

(65) Prior Publication Data

US 2009/0302092 A1 Dec. 10, 2009

Related U.S. Application Data

(60) Provisional application No. 61/058,666, filed on Jun. 4, 2008.

(51) Int. Cl.
*A61B 17/068* (2006.01)
(52) U.S. Cl. .............. 227/176.1; 227/19; 227/180.1; 606/219
(58) Field of Classification Search .............. 227/19, 227/176.1, 180.1, 178.1; 606/139, 219
See application file for complete search history.

(56) References Cited

U.S. PATENT DOCUMENTS

| | | | |
|---|---|---|---|
| 4,881,545 A | 11/1989 | Isaacs et al. | |
| 5,242,457 A * | 9/1993 | Akopov et al. | ............... 606/144 |
| 5,653,373 A * | 8/1997 | Green et al. | ............... 227/175.1 |
| 5,662,260 A * | 9/1997 | Yoon | ........................ 227/176.1 |
| 5,964,394 A | 10/1999 | Robertson | |
| 6,045,560 A | 4/2000 | McKean et al. | |
| 6,817,508 B1 | 11/2004 | Racenet et al. | |
| 7,070,083 B2 | 7/2006 | Jankowski | |
| 7,237,708 B1 | 7/2007 | Guy et al. | |
| 7,278,563 B1 * | 10/2007 | Green | ........................ 227/180.1 |
| 7,401,721 B2 * | 7/2008 | Holsten et al. | ............. 227/176.1 |
| 7,472,814 B2 * | 1/2009 | Mastri et al. | ............... 227/175.2 |
| 2006/0163312 A1 | 7/2006 | Viola et al. | |
| 2008/0078800 A1 | 4/2008 | Hess et al. | |

FOREIGN PATENT DOCUMENTS

| | | |
|---|---|---|
| GB | 2029754 | 3/1980 |
| WO | WO 02/30296 | 4/2002 |
| WO | WO 2006/055385 | 5/2006 |

OTHER PUBLICATIONS

European Search Report EP 09251240 dated Oct. 5, 2009. (8 pages).

* cited by examiner

*Primary Examiner* — Scott A. Smith

(57) ABSTRACT

An end effector for a surgical fastener applying instrument including a first jaw member and a second jaw member. The second jaw member includes first and second cartridges each containing a plurality of surgical fasteners, wherein each of the first and second cartridges is configured to move independently with respect to the first jaw member between a proximal position and a distal.

6 Claims, 5 Drawing Sheets

SURGICAL STAPLING INSTRUMENT WITH INDEPENDENT SEQUENTIAL FIRING

This application claims priority to U.S. provisional application No. 61/058,666, filed Jun. 4, 2008, the entire contents of which are incorporated herein by reference.

BACKGROUND

1. Technical Field

The present disclosure relates generally to surgical instruments and, more specifically, to surgical instruments for clamping, cutting, and fastening tissue.

2. Background of Related Art

Surgical stapling instruments used for applying parallel rows of staples through compressed living tissue are well known in the art. These surgical instruments are commonly employed for closing tissue or organs prior to transection or resection, for occluding organs in thoracic and abdominal procedures, and for fastening tissue in anastomoses.

Typically, such surgical stapling instruments include an anvil assembly, a cartridge assembly for supporting an array of surgical staples, an approximation mechanism for approximating the anvil and cartridge assemblies, an alignment or guide pin assembly for capturing tissue between the cartridge and anvil assemblies and for maintaining alignment between the cartridge and anvil assemblies during approximation and firing, and a firing mechanism for ejecting the surgical staples from the cartridge assembly through tissue and into contact with the anvil.

In use, a surgeon generally initially advances the alignment pin assembly and subsequently approximates the anvil and cartridge members. In some instruments, the alignment pin is advanced when the cartridge and anvil members are approximated. Next, the surgeon can fire the instrument to place staples in tissue. Additionally, the surgeon may use the same instrument or a separate instrument to cut the tissue adjacent or between the row(s) of staples.

SUMMARY

The present disclosure provides in one aspect an end effector for a surgical fastener applying instrument. The end effector includes a first jaw member and a second jaw member. The second jaw member includes first and second cartridges each containing a plurality of surgical fasteners, wherein each of the first and second cartridges is configured to move independently with respect to the first jaw member between a proximal position and a distal position.

The end effector can include a knife movable from a proximal position to a distal position. Preferably, the surgical fasteners are arranged in substantially linear rows. In some embodiments, the first and second cartridges are contained within a housing configured to be mountable on the surgical fastener applying instrument.

In some embodiments, the surgical fasteners comprise surgical staples, and the second jaw member is an anvil assembly configured to deform the staples.

The present disclosure provides in another aspect a surgical fastener applying instrument comprising a handle portion, an elongate portion extending distally from the handle portion, a first jaw member positioned at a distal portion of the instrument, and a second jaw member positioned at the distal portion of the instrument and including first and second cartridges. Each of the first and second cartridges includes a plurality of surgical fasteners contained therein and is configured to move independently with respect to the first jaw member between a proximal position and a distal position.

Preferably, the elongate portion defines a longitudinal axis and each of the first and second jaw members includes a tissue contacting surface oriented substantially perpendicular to the longitudinal axis of the elongate portion.

The instrument may further include a knife disposed between the first and second cartridges, wherein the knife is adapted to move from a proximal position to a distal position.

In one embodiment, the handle portion includes a first handle and a second handle, the first handle operatively associated with a first firing mechanism to advance the fasteners from the first cartridge and the second handle operatively associated with a second firing mechanism to advance the fasteners from the second cartridge, with the fasteners preferably arranged in substantially linear rows.

In one embodiment, the handle portion comprises first and second handles operatively connected to a thrusting assembly, the thrusting assembly movable in a first plane to advance the first cartridge and movable in a second plane to advance the second cartridge. In one embodiment, the thrusting assembly is movable in a first plane to fire the fasteners from the first cartridge and movable in a second plane to fire the fasteners from the second cartridge.

In one embodiment, the instrument includes a thrusting assembly for moving the first and second cartridges distally and for firing the fasteners from the first and second cartridges, the thrusting assembly having a first set of protrusions configured to actuate the first cartridge and a second set of protrusions transversely out of alignment with the first set of protrusions and configured to actuate the second cartridge.

The present disclosure also provides in another aspect a disposable loading unit for mounting to a surgical fastener applying instrument, the disposable loading unit comprising a first cartridge containing a first plurality of surgical fasteners and a first set of fastener pushers and a second cartridge movable with respect to the first cartridge and containing a second plurality of surgical fasteners and a second set of fastener pushers.

In one embodiment, an anvil is connected to at least the first cartridge. The disposable loading unit can optionally include a knife. The disposable loading unit can include a housing configured to contain the first and second cartridges. Preferably, the plurality of fasteners are arranged in substantially linear rows.

BRIEF DESCRIPTION OF FIGURES

Various embodiments of the presently disclosed surgical stapling instrument are disclosed herein with reference to the drawings, wherein.

DETAILED DESCRIPTION

Figure 1:
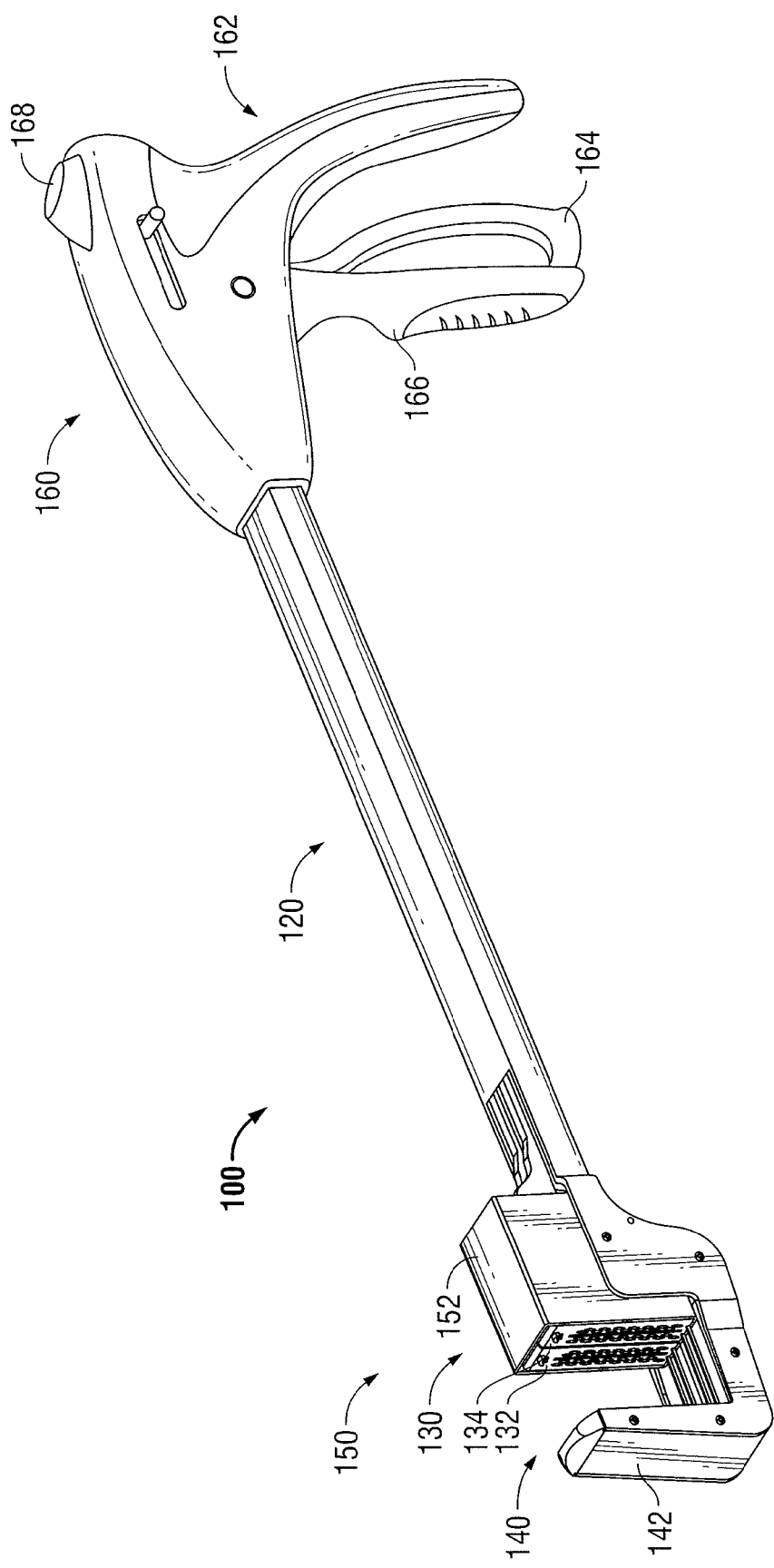
FIG. 1 is a perspective view of an embodiment of the surgical stapling instrument of the present disclosure with the first and second cartridges in a proximal position.

Embodiments of the presently disclosed surgical stapling instrument are described in detail with reference to the drawings, wherein like reference numerals designate similar or identical elements in each of the several views. In the drawings and the description that follows, the term "proximal" refers to the end of the surgical stapling instrument that is closer to the operator, whereas the term "distal" refers to the end of the surgical stapling instrument that is further from the operator. As appreciated by one skilled in the art, the depicted surgical stapling instrument fires staples, but it may be adapted to fire any other suitable fastener such as clips and two-part fasteners.

With reference to FIG. 1, reference numeral 100 designates an embodiment of the presently disclosed surgical stapling instrument. In the interest of brevity, the present disclosure focuses on an end effector of surgical stapling instrument 100. U.S. Provisional Patent Application Ser. No. 61/050,272, filed on May 5, 2008, and U.S. patent application Ser. No. 11/786,198, filed on Apr. 10, 2007 describe in detail the structure and operation of similar surgical stapling instruments. The entire contents of these applications are incorporated herein by reference.

Figure 3:
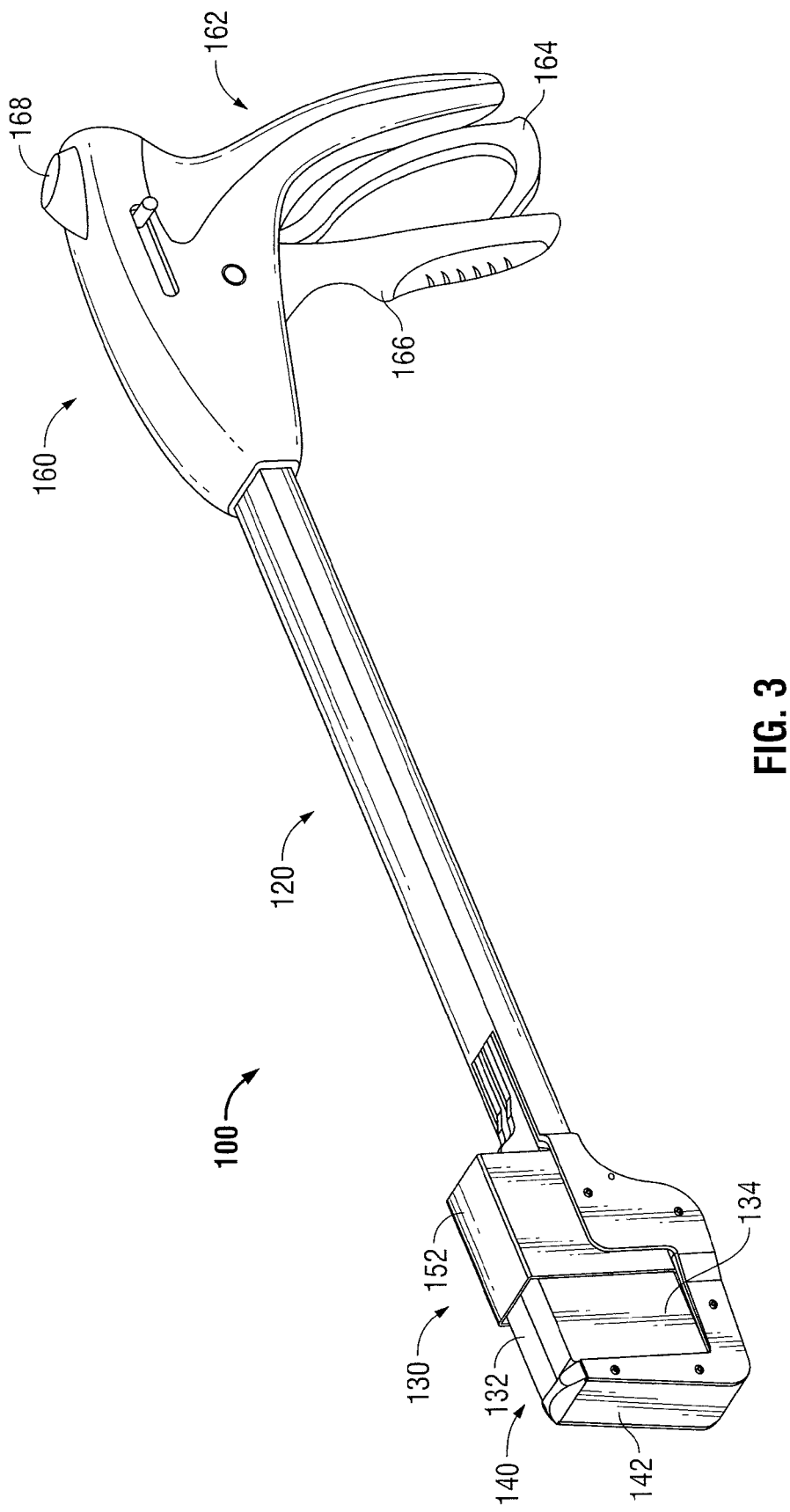
FIG. 3 is a perspective view of the surgical stapling instrument of FIG. 1 with the first and second cartridges located in a distal (approximated) position.

Surgical stapling instrument 100 is configured to clamp, fasten, and/or cut tissue. In general, surgical stapling instrument 100 includes a handle portion 160, an elongate portion 120 extending distally from the handle portion 160, and an end effector 150 adapted to clamp and fasten tissue. Elongate portion 120 operatively couples handle portion 160 with end effector 150. End effector 150 is composed of a first jaw member 130 and a second jaw member 140. First jaw member 130 contains first and second cartridge assemblies 132, 134, while second jaw member 140 includes an anvil assembly 142. The anvil assembly 140 includes a plurality of anvil pockets or depressions to form the fasteners when the fasteners are advanced into contact with the anvil pockets. As thoroughly discussed below, first and second cartridge assemblies 132, 134 are configured to move independently from a proximal or open (unapproximated) position, as seen in FIG. 1, to a distal or approximated position, as shown in FIG. 3, upon actuation of handle portion 160. Although a single anvil assembly is shown, it is also contemplated that two anvil assemblies could be provided, each cooperating with a respective cartridge assembly.

Handle portion 160 includes a stationary handle 162, a first movable handle 164, a second movable handle 166, and a release button 168. First movable handle 164 shares a pivot point with second movable handle. Each of first and second movable handles 164, 166 is configured to move pivotally toward or away from stationary handle 162. First movable handle 164 is operatively connected to second cartridge assembly 134 through a mechanism adapted to convert an actuation of first movable handle 164 into a distal translation of second cartridge assembly 134. Similarly, second movable handle 166 is operatively associated with first cartridge assembly 132 through a mechanism configured to convert an actuation of second movable handle 166 into a distal translation of first cartridge assembly 132. As recognized by one skilled in the art, any conventional translation mechanism may be employed to operatively couple first movable handle 164 to second cartridge assembly 134 and second movable handle 166 to first cartridge assembly 132. Release button 168 is disposed in mechanical cooperation with the translating mechanisms coupled to first and second cartridge assemblies 132, 134. During operation, the depression of release button 168 unlocks the translation mechanisms connected to first and second cartridge assemblies 132, 134, causing first and second cartridge assemblies 132, 134 to return to their proximal positions. An example of such release button 168 is disclosed in U.S. Pat. No. 6,817,508, the entire contents of which are incorporated herein by reference. It should be appreciated that the pivoting handles illustrate one method of approximating the cartridge assemblies, it being understood that other approximation mechanisms could be utilized such as a lever on top of the body portion or a longitudinally slidable member.

When first and second cartridge assemblies 132, 134 are in their proximal positions (as shown in FIG. 1), a housing 152 of end effector 150 covers at least a portion of first and second cartridge assemblies 132, 134. The housing 152 has a distal opening to allow exit (distal movement) of the cartridge from the housing 152. By providing the housing 152, cartridge assemblies can be more easily removed and inserted as a single unit. That is, the two cartridges can be contained in the housing, and the housing can be packaged separately with the instrument, or packaged with the instrument, and removable and replaceable with another housing (e.g. after firing) so a new housing with two cartridges containing staples can be mounted to the instrument. The housing could also include a knife and/or an anvil assembly for forming the fasteners.

First and second cartridge assemblies 132, 134 each has a tissue contacting surface oriented substantially perpendicular or transverse to a longitudinal axis defined along elongate portion 120. First and second cartridge assemblies 132, 134 both contain retention slots adapted to accommodate staples or any other suitable fasteners. In one embodiment, these retention slots are arranged in substantially linear rows. The translation mechanisms operatively coupled to first and second cartridge assemblies 132, 134 not only translate first and second cartridge assemblies independently of each other toward anvil assembly 142 but also advance staple pushers to eject the staples housed in the retention slots. The staple pushers are positioned within first and second cartridge assemblies 132, 134 and are configured for deploying the staples from the retention slots. During ejection, the staples advance through tissue toward and into contact with anvil assembly 142 to fasten tissue.

Anvil assembly 142 includes a tissue contacting surface oriented substantially perpendicular or transverse relative to the longitudinal axis defined by elongate portion 120. In one embodiment, the tissue contacting surface of anvil assembly 142 define concavities or staple pockets (not shown) to deform the leg of the staples ejected from first and second cartridge assemblies 132, 134 and form the fasteners. In a preferred embodiment, each cartridge has two substantially linear rows of staples and the anvil has four substantially linear rows of staple pockets. Clearly, fewer or greater number of staple rows and cooperating staple pockets could be provided.

In addition to anvil assembly 142, end effector 150 may include knife 306 (see FIG. 5) positioned between first and second cartridge assemblies 132, 134. During operation of surgical stapling instrument 100, knife 306 may be advanced from a proximal position to a distal position by a translation mechanism operatively connected to handle portion 160, as discussed in detail below. When knife 306 moves distally, the knife 306 cuts through tissue. The knife can be moved independently of the firing of the staples or in conjunction therewith.

In operation, surgical stapling instrument 100 sequentially clamps and fastens tissue. In one embodiment, surgical stapling instrument 100 also severs tissue, as explained above.

Figure 2:
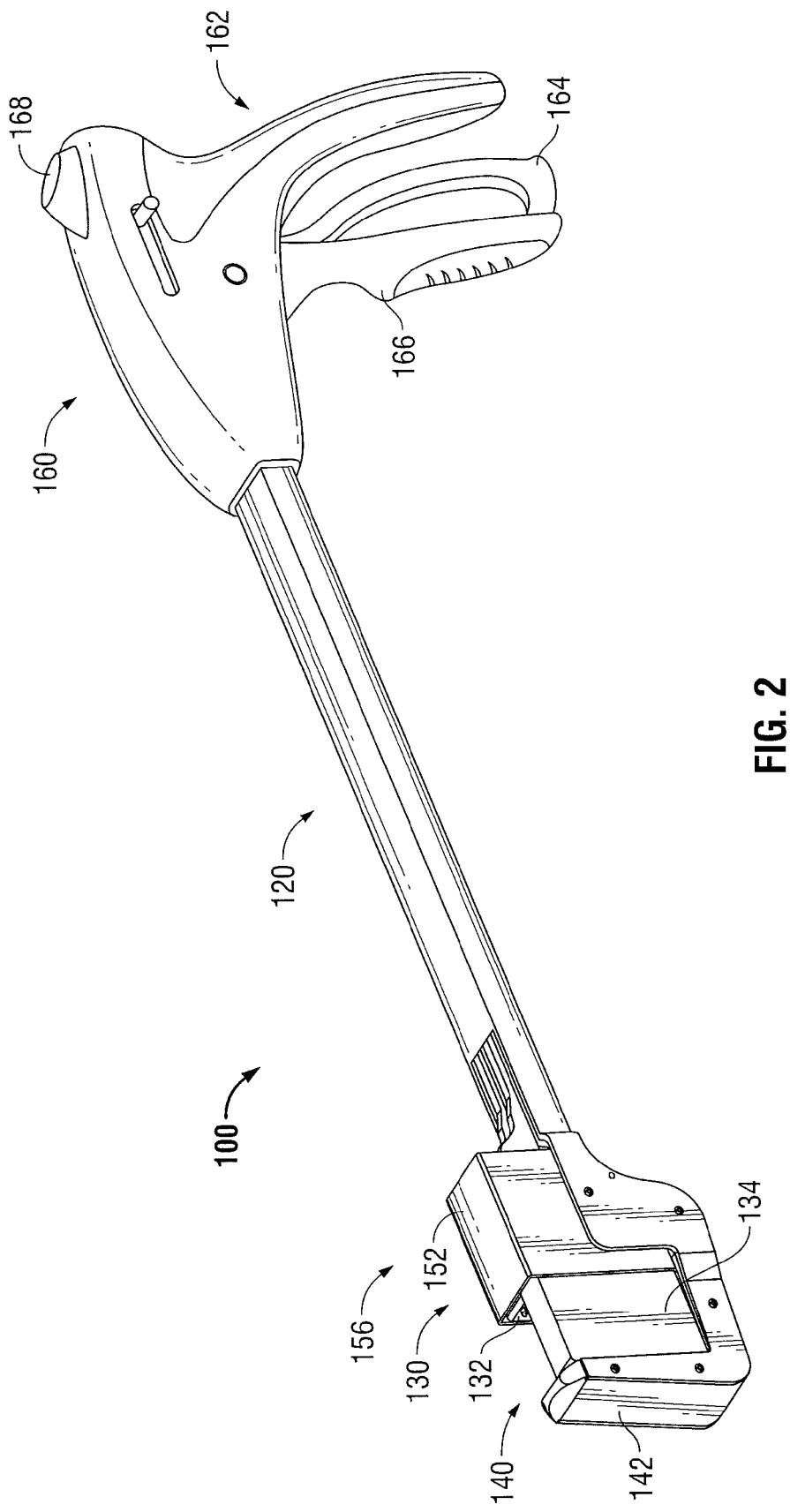
FIG. 2 is a perspective view of the surgical stapling instrument of FIG. 1 with the first cartridge located in a distal (approximated) position.

Initially, an operator maneuvers surgical instrument 100 inside or outside a patient's body to place the target tissue between first and second jaw members 130, 140, while first and second cartridge assemblies 132, 134 are located in their proximal positions, as depicted in FIG. 1. The user then pivots first movable handle 164 toward stationary handle 162 to translate second cartridge assembly 134 from a proximal position to a distal position, as shown in FIG. 2. Since first movable handle 164 is operatively associated with second cartridge assembly 134 through the translation mechanism, actuating first movable handle 164 moves second cartridge assembly 134 distally. As second cartridge assembly 134 translates in a distal direction, it clamps the target tissue between the cartridge and the anvil assembly 142. Due to the operative relationship between the translation mechanism connected to first movable handle 164 and the staple pushers located within second cartridge assembly 134, continued movement of first movable handle 164 toward stationary handle 162 ejects the staples from the second cartridge assembly 134. Alternatively, a separate actuator could be provided to fire the staples. Once ejected, the staples fasten the tissue clamped by second cartridge assembly 134 as they are deformed by the anvil, thereby fastening a section of the target tissue.

After firing the staples in the second cartridge assembly 134 and before firing the staples in first cartridge assembly 132, the physician may perform other medical operations. For example, if the surgeon is conducting a lower anterior resection, the surgeon may execute a rectal washout. Alternatively, the surgeon may apply therapies to the operative site. As discussed hereinabove, an embodiment of surgical stapling instrument 100 includes knife 306 positioned between first and second cartridge assemblies 132, 134. When employing the stapler of this embodiment, the surgeon may transect or cut the tissue located between first and second jaw members 130, 140 before actuating the first cartridge assembly 132. In any event, the sequential operation of the two cartridges of the surgical stapling instrument 100 allows the surgeon to perform other medical procedures or treatment before firing first cartridge assembly 132. Continued pivotal movement of first movable handle 164 toward stationary handle 162 after staple ejection and formation, in certain embodiments, actuates knife 306. If a knife is not provided, the surgeon may optionally transect the tissue with a separate instrument.

To fire the staples in first cartridge assembly 132, the user pivots second movable handle 166 toward stationary handle 162. In doing so, the translation mechanism operatively connected to second movable handle 166 translates first cartridge assembly from a proximal position to a distal position, as shown in FIG. 3. When first cartridge assembly 132 moves to the distal position, it clamps a portion of the tissue positioned between first and second jaw members 130, 140. Since the translation mechanism operatively associated with the second movable handle 164 is also coupled to the staple pushers located in the first cartridge assembly 132, continued actuation of second movable handle 164 moves these staple pushers distally, causing the ejection of the staples housed in first cartridge assembly 132. Alternatively, a separate actuator could be provided to fire the staples. The staples fired from first cartridge assembly 132 consequently fasten the tissue located between first and second jaw members 130, 140. After firing the staples from the first and second cartridge assemblies 132, 134, the operator presses release button 168 to retract first and second cartridge assemblies to their proximal positions and release first and second movable handles 164, 166, to the position shown in FIG. 1.

Although FIGS. 1-3 illustrate the use of surgical stapling instrument 100 in particular firing sequence, users may utilize surgical stapling instrument 100 in other firing sequences. A user, for instance, may initially actuate first movable handle 164 to approximate second cartridge assembly 134 to anvil assembly 142 and deploy the staples stored in second cartridge assembly 134. Then, the user actuates second movable handle 166 to move first cartridge assembly 132 distally and fire the staples located within first cartridge assembly 132. Following the ejection of the staples in first and second cartridge assemblies 132, 134, the user transects the target tissue with knife 306 located between the first and second cartridge assemblies 132, 134. A separate translation mechanism may be employed to move knife 306 distally. This translation mechanism may be operatively connected to first movable handle 164, second movable handle 166, or another actuation mechanism. In a preferred embodiment, the staples can be fired substantially simultaneously. Alternatively, firing can be staggered to distribute the firing forces.

Surgical stapling instrument 100 may include other translation mechanisms to allow other firing sequences. In one embodiment of surgical stapling instrument 100, an operator first translates distally first cartridge assembly 132 by actuating second movable handle 166. Thereafter, the operator actuates first movable handle 164 to simultaneously fire the staples of first cartridge assembly 132 and move distally second cartridge assembly 134. The operator then further actuates first movable handle 164 to eject the staples of second cartridge assembly 134. Subsequently, the knife is translated distally to cut the tissue located between first and second jaw members 130, 140.

Another embodiment of the surgical stapling instrument 100 employs a firing sequence, wherein the user initially moves first cartridge assembly 132 in a distal direction and fires the staples housed therein by a single actuation of second movable handle 166. Then, the user actuates first movable handle 164 once to approximate second cartridge assembly 134 toward anvil assembly 142 and eject the staples of second cartridge assembly 134. After deploying (ejecting) the staples of second cartridge assembly 134, the user moves knife 306 distally to transect tissue.

In still another embodiment, the firing sequence of surgical stapling instrument 100 includes initially moving first cartridge assembly 132 distally by actuating second movable handle 166 and then simultaneously ejecting the staples of first staple cartridge 132 and translating distally second cartridge assembly 134 with further actuation of second movable handle 166. Subsequently, the user actuates first movable handle 164 to simultaneously fire the staples of second cartridge assembly 134 and move knife 306 in a distal direction to cut tissue.

Surgical stapling instrument 100 may also be employed in the following firing sequence. The operator first actuates second movable handle 166 once for moving distally first cartridge assembly 132 and ejecting the staples housed therein. Then, the operator actuates first movable handle 164 once for moving distally the second cartridge assembly 134 and ejecting the staples housed therein.

It should also be appreciated that other actuation mechanisms can be utilized to provide other firing sequences. For example, a separate actuator could be provided to fire the staples of the first cartridge and/or second cartridge after approximation. That is, for example, a first actuator, such as a handle, rotatable knob, lever, or slider can be utilized to approximate the first cartridge, a second actuator, such as a handle, rotatable knob, lever or slider can be utilized to approximate the second cartridge and a) a third actuator can be utilized to fire the fasteners of the first and second cartridge or b) a third actuator can be utilized to fire the fasteners of the first cartridge and a fourth actuator can be utilized to fire the fasteners of the second cartridge. A knife can be provided which can be actuated independently by a fifth actuator or configured to advance upon movement of any of the aforementioned actuators.

Figure 4:
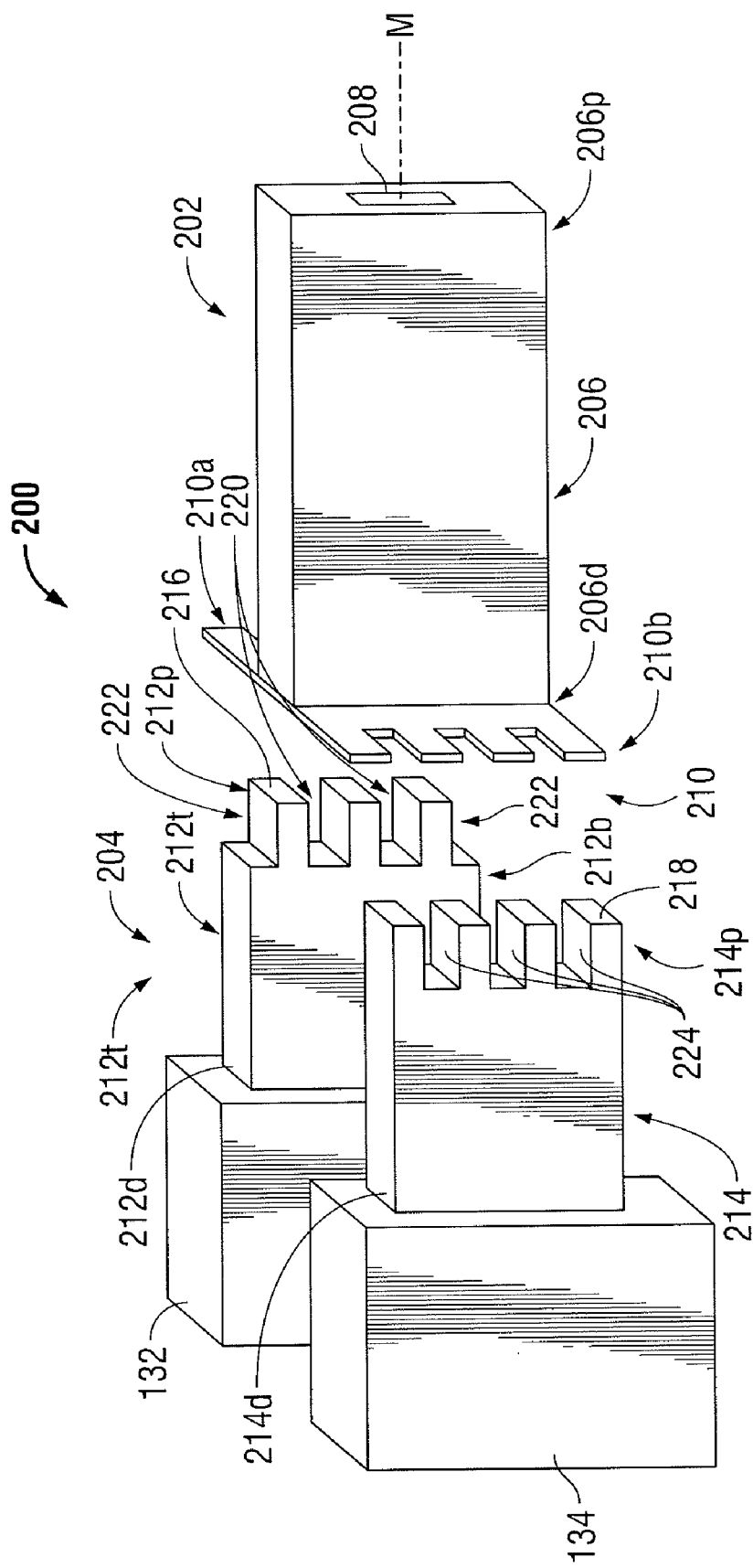
FIG. 4 is a perspective view of one embodiment of a translation mechanism for the first and second cartridges.

Surgical stapling instrument 100 may include a variety of translation mechanisms for performing the firing sequences described above. FIG. 4 illustrates one example of a translating mechanism that allows sequential translation and firing of first and second cartridge assemblies 132, 134 of surgical stapling instrument 100. Translation mechanism 200, which is located within surgical stapling instrument 100, includes a single thrusting assembly 202 and a dual thrusting assembly 204.

Single thrusting assembly 202 is operatively connected to first and second movable handles 164, 166 and contains a main body 206 having proximal and distal ends 206p, 206d. Main body 206 defines a longitudinal axis M extending along its length and includes a longitudinal opening 208 extending from proximal end 206p to distal end 206d. Longitudinal opening 208 is configured for receiving knife 306 and is preferably oriented substantially parallel to longitudinal axis M. Single thrusting assembly 202 further includes a plurality of fingers 210 protruding from distal end 206d of main body 206. Fingers 210 are oriented transverse or substantially perpendicular to longitudinal axis M. In the depicted embodiment, single thrusting assembly 202 includes a first set of three fingers 210a extending in one direction transverse to longitudinal axis and another set of four fingers 210b extending in an opposing direction transverse to longitudinal axis M. It is envisioned, however, that single thrusting member 202 may have fewer or greater number of fingers 210. In operation, fingers 210 of single thrusting assembly 202 contact and advance dual thrusting assembly 204 upon actuation of first or second movable handles 164, 166.

Dual thrusting assembly 204 includes first and second thrust members 212, 214 adapted to displace first and second cartridge assemblies 132, 134 distally and to fire the fasteners from the respective cartridge. Each of the first and second thrusting members 212, 214 includes respective proximal and distal ends 212p, 214p and 212d, 214d. Distal ends 212d, 214d of first and second thrusting members 212, 214 are operatively connected to first and second cartridge assemblies 132, 134, respectively. Consequently, first and second thrusting members 212, 214 translate first and second cartridge assemblies distally, when fingers 210 of single thrust assembly 202 push the respective thrust members sequentially in a distal direction. First and second thrust members also are advanced to fire the fasteners from the cartridge. For engagement with fingers 210 of single thrust assembly 202, each of the first and second thrust members 212, 214 includes respective protrusions 216, 218 extending proximally therefrom.

In the embodiment shown in FIG. 4, first thrust member 212 contains three protrusions 216 spaced apart from one another and defining spaces 220 therebetween. Protrusions 216 are dimensioned to receive fingers 210a of single thrusting assembly 202. Besides spaces 220, first thrust member 212 defines additional spaces 222 on top and bottom portions 212t, 212b thereof.

Like first thrusting member 212, second thrusting member 214 also includes protrusions 218 spaced apart from one another and defining spaces 224 therebetween. Second thrusting member 214 in this embodiment has four protrusions 218 and lacks spaces on the top and bottom portions thereof. Protrusions 218 are configured to receive fingers 210b of single thrusting assembly 202. As seen in FIG. 4, protrusions 218 of second thrusting member 214 are transversely aligned with spaces 220 of first thrusting member 212 and protrusions 216 of first thrusting member 212 are transversely aligned with spaces 224 of second thrusting member 214.

During operation, single thrusting assembly 202 is movable between a first position, where fingers 210a of single thrusting assembly 202 are longitudinally aligned with protrusions 216 of first thrusting member 212, and a second position, where fingers 210b are longitudinally aligned with protrusions 218 of second thrusting member 214. Accordingly, spaces 220 and 222 of first thrusting member 212 receive fingers 210a, when single thrusting assembly 202 is located in the second position. Conversely, spaces 224 of second thrusting member 214 receive fingers 210b, when single thrusting assembly 202 is situated in the first position. Consequently, single thrusting assembly 202 advances initially in a first plane so that fingers 210a engage protrusions 216 of the first thrusting member 212 to advance thrusting member 212 to approximate the cartridge 132 and to subsequently fire the staples as the thrusting member distal end engages staple pushers positioned in the cartridge 132 or engages a firing member within the cartridge which in turn engages the pushers. In this position of thrusting member 212, fingers 210b are received within spaces 224 of second thrusting member 214 so there is no advancement of thrusting member 214.

After firing of cartridge 132, single thrusting assembly 202 is shifted to a second plane, parallel to the first plane. In this second plane, single thrusting assembly 202 is advanced to approximate and subsequently fire cartridge 134 as fingers 210b can now engage protrusions 218 of second thrusting member 214 to advance it distally so that its contact with the cartridge 134 moves it distally and its further advancement causes its distal end to engage the plurality of pushers or a firing member engageable with the pushers contained within the cartridge 134. As with the first thrusting member 212, the pushers engage the staples and eject them from the cartridge 134 in a distal direction toward and into contact with the opposing anvil. In this position of the second thrusting member 214 to advance the cartridge 134 and fire the staples contained therein, fingers 210a are received within spaces 220 of first thrust member 212 so that it is not advanced by the single thrusting assembly 202. Movement of the single thrusting assembly 202 from the first to the second plane can be achieved for example by having the bottom surface of main body 206 slide within a stepped channel (not shown) such that the top surface of the channel has a first plane to accommodate movement of the main body 206 in the first plane and a second upper (or alternatively lower) plane to accommodate movement of the main body 206 in the second plane.

Various actuators can be utilized to advance single thrusting assembly 202. In one example, the actuation of first movable handle 164 translates single thrusting assembly 202 in a distal direction so that fingers 210a engage and displace protrusions 216 distally, whereas fingers 210b slide into spaces 224 of second thrusting member 214. As a result of the distal translation of protrusions 216 of first thrusting member 212, first cartridge assembly 132 moves toward anvil assembly 142 and clamps tissue, followed by advancement of the fasteners from the cartridge into contact with the anvil. Subsequently, actuation of second movable handle 166 further advances thrusting assembly 2002 and positions single thrusting assembly 202 in the second position (e.g. in a different plane) and moves single thrusting assembly 202 distally. When single thrusting assembly 202 moves distally while located in the second position, fingers 210b engage and drive protrusions 218 of second thrusting member 214, whereas fingers 210a slide into spaces 220 and 222 of first thrusting member 212. As a result of the distal translation of protrusions 218 of second thrusting member 214, second cartridge assembly 134 moves toward anvil assembly 142 and clamps tissue, followed by advancement of the fasteners from the cartridge into contact with the anvil. Note, alternatively, movement of the single thrusting assembly 202 to the second position (plane) could be achieved by a mechanism other than by the second handle 166.

Figure 5:
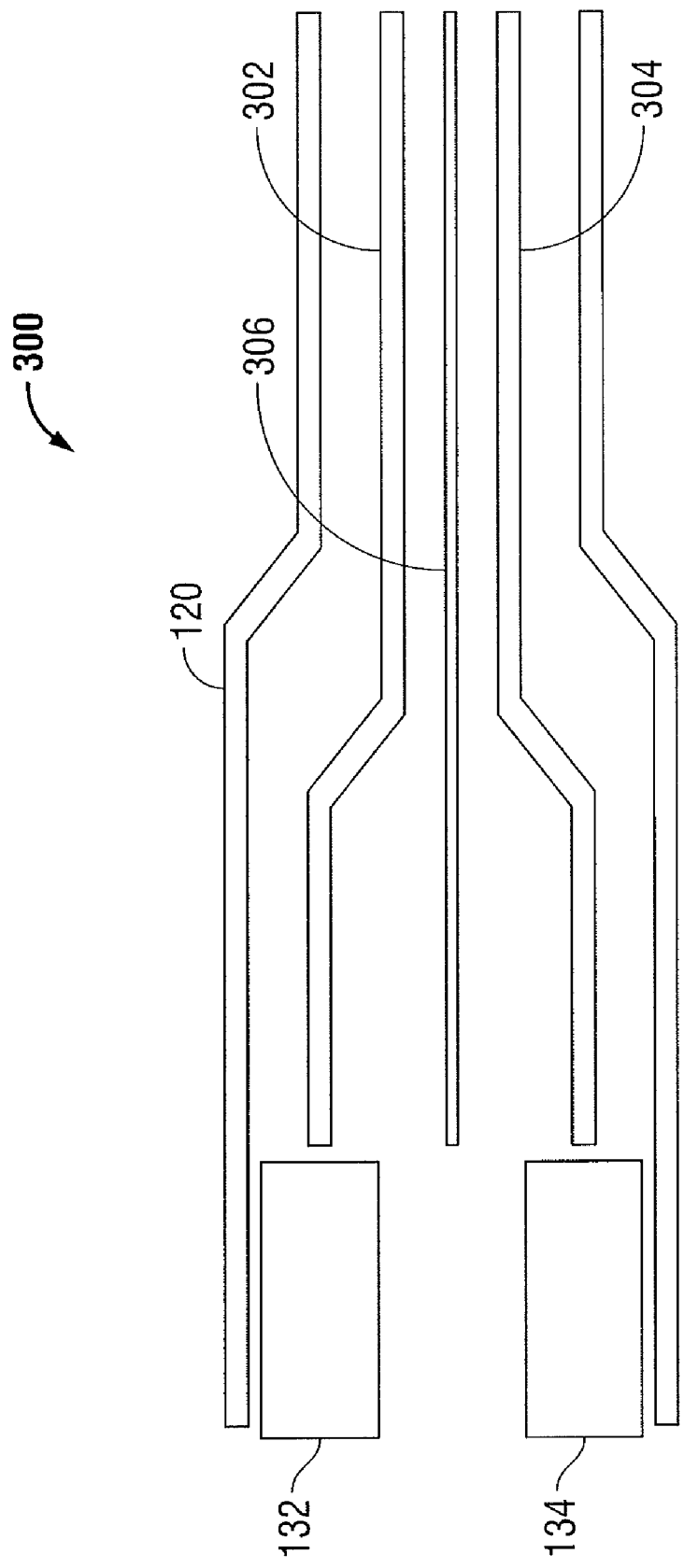
FIG. 5 is a schematic top view of an alternate embodiment of a firing mechanism of the surgical stapling instrument of FIG. 1.

FIG. 5 shows another embodiment of a translation mechanism 300 for surgical stapling instrument 100. In general, translation mechanism 300, which is partially located within elongate portion 120 of surgical stapling instrument 100, includes a first firing bar 302 and a second firing bar 304. First firing bar 302 is operatively connected to first movable handle 164, while second firing bar 304 is operatively connected to second movable handle 166. First and second firing bars 302, 304 are independently movable. In particular, first firing bar 302 is configured to translate distally upon actuation of first movable handle 164. As first firing bar 302 moves distally, it pushes first cartridge assembly 132 distally and the moves the staples pushers contained within the first cartridge assembly 132 distally to eject the staples housed in first cartridge assembly 132. Second firing bar 304 is configured to move distally upon actuation of second movable handle 166. As second firing bar 304 moves distally, it pushes second cartridge assembly 134 distally and moves the staple pushers within cartridge assembly 134 distally to eject the staples located within second cartridge assembly 134. In the embodiment shown in FIG. 5, surgical stapling instrument further includes knife 306 operatively associated with either first or second movable handles 164, 166. Knife 306 is configured to translate distally in response to an actuation of either first or second movable handles 164, 166 or another actuation mechanism which can move knife independently of movement or firing of the cartridges.

The present disclosure also includes a method of using the surgical stapling instruments described above. The method includes the steps of providing a surgical stapling instrument, advancing the first cartridge to approximate the jaw members to clamp tissue, firing the staples (fasteners) from the first cartridge, advancing the second cartridge to approximate the jaw members to clamp tissue, and firing the staples (fasteners) from the second cartridge. The method may also include the steps of advancing a guide pin, transecting tissue, and releasing the guide pin.

The present disclosure also relates to another method of using the described surgical instrument. The method, as described above, includes providing a surgical instrument, clamping tissue via approximation of the first cartridge with the anvil, firing staples (e.g., simultaneously) from the first cartridge, cutting tissue (e.g., with a knife disposed in mechanical cooperation with the surgical instrument, or using a separate instrument), and clamping tissue via approximation of the second cartridge with the anvil, and firing staples (e.g., simultaneously) from the second cartridge. In certain embodiments, the instrument can be used for lower anterior resection. First, the first cartridge is actuated, clamping onto intestinal tissue. Then, the interior of the intestinal tissue is washed out or otherwise cleansed. The tissue is then cut and stapled with the first cartridge. Next the second cartridge is advanced and fired to advance a second set of staples into the tissue. In this way, the interior intestinal tissue is cleansed up to the location of the first cartridge, including the area where the jaws will engage the intestinal tissue to be stapled and/or cut, once the jaws are approximated.

The present disclosure also relates to a loading unit configured for releasable engagement with a surgical instrument, the loading unit including first and second jaw members and configured for releasable engagement with a distal portion of the surgical instrument. The loading unit can also include a knife. At least one of the jaw members is movable with respect to the other between an open position and an approximated position for engaging body tissue therebetween. The first jaw member includes first and second separate cartridges. Alternatively, the loading unit could include only the first jaw member containing first and second cartridges mountable to the instrument.

It will be understood that various modifications may be made to the embodiments of the presently disclosed surgical stapling instruments. For instance, an embodiment of the presently disclosed surgical stapling instrument includes an alignment pin or guide pin in each cartridge assembly for capturing tissue between the cartridge and anvil assemblies. In another embodiment, the first cartridge assembly is operatively connected to the first movable handle, and the second movable handle is operatively connected to the second movable handle. Therefore, there above description should not be construed as limiting, but merely as exemplifications of embodiments. Those skilled in the art will envision other modifications within the scope and spirit of the present disclosure.

What is claimed is:
1. A surgical fastener applying instrument, comprising:
a handle portion;
an elongate portion extending distally from the handle portion;
a first jaw member positioned at a distal portion of the instrument; and
a second jaw member positioned at the distal portion of the instrument and including first and second cartridges, wherein each of the first and second cartridges includes a plurality of surgical fasteners contained therein and is configured to move independently with respect to the first jaw member between a proximal position and a distal position, wherein the handle portion includes a first handle and a second handle, the first handle operatively associated with a first firing mechanism to advance the fasteners from the first cartridge and the second handle operatively associated with a second firing mechanism to advance the fasteners from the second cartridge, the fasteners arranged in substantially linear rows.
2. The surgical fastener applying instrument of claim 1, wherein the elongate portion defines a longitudinal axis and each of the first and second jaw members includes a tissue contacting surface oriented substantially perpendicular to the longitudinal axis of the elongate portion.
3. The surgical fastener applying instrument of claim 1, further comprising a knife disposed between the first and second cartridges, wherein the knife is adapted to move from a proximal position to a distal position.
4. A surgical fastener applying instrument, comprising:
a handle portion;
an elongate portion extending distally from the handle portion;
a first jaw member positioned at a distal portion of the instrument; and
a second jaw member positioned at the distal portion of the instrument and including first and second cartridges, wherein each of the first and second cartridges includes a plurality of surgical fasteners contained therein and is configured to move independently with respect to the first jaw member between a proximal position and a distal position, wherein the handle portion comprises first and second handles operatively connected to a thrusting assembly, the thrusting assembly movable in a first plane to advance the first cartridge and movable in a second plane to advance the second cartridge.

5. A surgical fastener applying instrument, comprising:

a handle portion;

an elongate portion extending distally from the handle portion;

a first jaw member positioned at a distal portion of the instrument; and a second jaw member positioned at the distal portion of the instrument and including first and second cartridges, wherein each of the first and second cartridges includes a plurality of surgical fasteners contained therein and is configured to move independently with respect to the first jaw member between a proximal position and a distal position, wherein the handle portion comprises first and second handles operatively connected to a thrusting assembly, the thrusting assembly movable in a first plane to fire the fasteners from the first cartridge and movable in a second plane to fire the fasteners from the second cartridge.

6. A surgical fastener applying instrument, comprising:

a handle portion;

an elongate portion extending distally from the handle portion;

a first jaw member positioned at a distal portion of the instrument;

a second jaw member positioned at the distal portion of the instrument and including first and second cartridges, wherein each of the first and second cartridges includes a plurality of surgical fasteners contained therein and is configured to move independently with respect to the first jaw member between a proximal position and a distal position;

a knife disposed between the first and second cartridges, wherein the knife is adapted to move from a proximal position to a distal position; and a thrust assembly for moving the first and second cartridges distally and for firing the fasteners from the first and second cartridges, the thrust assembly having a first set of protrusions configured to actuate the first cartridge and a second set of protrusions transversely out of alignment with the first set of protrusions and configured to actuate the second cartridge.

* * * * *